United States Patent [19]

Umemoto

[11] 4,371,710

[45] Feb. 1, 1983

[54] PERFLUOROALKYL COMPOUNDS AND PROCESS FOR PREPARING THE SAME

[75] Inventor: Teruo Umemoto, Sagamihara, Japan

[73] Assignee: Sagami Chemical Research Center, Tokyo, Japan

[21] Appl. No.: 303,322

[22] Filed: Sep. 17, 1981

Related U.S. Application Data

[63] Continuation of Ser. No. 156,951, Jun. 6, 1980, Pat. No. 4,324,741.

[30] Foreign Application Priority Data

Jun. 6, 1979 [JP] Japan ................................ 54-69979

[51] Int. Cl.³ .................. C07C 143/00; A61K 31/185
[52] U.S. Cl. ........................................ 568/35; 568/28; 424/315; 424/350
[58] Field of Search ..................................... 568/35, 28

[56] References Cited

U.S. PATENT DOCUMENTS 4,007,221  2/1977  Urbach ........................... 260/505 R
4,324,741  4/1982  Umemoto ....................... 260/505 R

*Primary Examiner*—Alan Siegel
*Attorney, Agent, or Firm*—Sughrue, Mion, Zinn, Macpeak & Seas

[57] ABSTRACT

Perfluoroalkyl compounds represented by the formula (I):

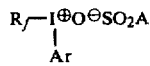

wherein $R_f$ represents a perfluoroalkyl group having 1 to 20 carbon atoms, Ar represents a substituted or unsubstituted phenyl group wherein the substituent is an alkyl group having 1 to 4 carbon atoms or a halogen atom, I represents an iodine atom, and A represents a perfluoroalkyl group having 1 to 20 carbon atoms which can be the same or different from $R_f$, a hydroxy group an alkyl group having 1 to 4 carbon atoms, an aryl group or a halogen atom, and processes for preparing the perfluoroalkyl compounds represented by the formula (I).

1 Claim, No Drawings

PERFLUOROALKYL COMPOUNDS AND PROCESS FOR PREPARING THE SAME

This is a continuation of application Ser. No. 156,951, filed June 6, 1980, now U.S. Pat. No. 4,324,741.

BACKGROUND OF THE INVENTION

1. Field of the Invention

This invention relates to novel perfluoroalkyl compounds and processes for preparing the same. More particularly, the present invention relates to the perfluoroalkyl compounds of the formula (I)

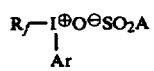
(I)

wherein $R_f$ represents a perfluoroalkyl group having 1 to 20 carbon atoms, Ar represents a substituted or unsubstituted phenyl group wherein the substituent is an alkyl group having 1 to 4 carbon atoms or a halogen atom, I represents an iodine atom, and A represents a perfluoroalkyl group having 1 to 20 carbon atoms which can be the same as or different from $R_f$, a hydroxy group, an alkyl group having 1 to 4 carbon atoms, an aryl group or a halogen atom, and process for preparing the same. The perfluoroalkyl compounds of the formula (I) are mainly useful as perfluoroalkyl group-introducing agents.

2. Brief Description of the Prior Art

The perfluoroalkyl compounds represented by the formula (I) are useful as perfluoroalkyl group-introducing agents. For example, these compounds can be reacted with 2(1H),3(4H)-quinoxalinedione or a salt thereof which is commercially available to produce 6-perfluoroalkyl-2(1H), 3(4H)-quinoxalinedione compounds useful as hypnotic agents as disclosed in U.S. Pat. No. 3,992,378. (Refer to Reference Examples hereinafter described.)

Hitherto, it was known that, for example, 6-pentafluoroethyl-2(1H),3(4H)-quinoxaline can be prepared by reacting p-bromonitrobenzene with pentafluoroethyl iodide in the presence of copper to produce p-pentafluoroethylnitrobenzene which is then subjected to reduction, acetylation, nitration, deacetylation and reduction to produce 4-pentafluoroethyl-O-phenylenediamine, and reacting the diamine with diethyl oxalate, as described in German DT 2,606,982 and U.S. Pat. No. 3,992,378. However, the above conventional process requires multiple reaction steps and is therefore not considered as advantageous process in practicing on an industrial scale.

DETAILED DESCRIPTION OF THE INVENTION

As a result of extensive studies on perfluoroalkyl group-introducing agents, the present inventor found that the perfluoroalkyl compounds of the formula (I) can be easily prepared by the process according to the present invention.

The perfluoroalkyl compounds (I) of the present invention are very useful in a wide variety of utilities for perfluoroalkylation. For example, the perfluoroalkylthio compounds obtained by reacting the perfluoroalkyl compounds (I) with a mercapto compound, for example, pentafluoroethylthioacetic acid, can be used as a modifying agent for cephalosporin compounds. Also, these perfluoroalkylthio compounds are useful as surface active agents and fiber treating agents.

The present invention is therefore to provide perfluoroalkyl compounds represented by the formula (I)

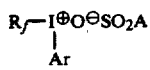
(I)

wherein $R_f$ represents a perfluoroalkyl group having 1 to 20 carbon atoms, Ar represents a substituted or unsubstituted phenyl group wherein the substituent is an alkyl group having 1 to 4 carbom atoms or a halogen atom, I represents an iodine atom, and A represents a perfluoroalkyl group having 1 to 20 carbon atoms which can be the same or different from $R_f$, a hydroxy group, an alkyl group having 1 to 4 carbon atoms, an aryl group or a halogen atom, and processes for preparing the perfluoroalkyl compounds of the formula (I) above which can be easily applied to the production on an industrial scale.

The term "aryl" as used herein for the substituent A means an unsubstituted or substituted phenyl group wherein the substituent is a halogen atom or a nitro group.

The term "halogen" as used herein means a fluorine, chlorine, bromine or iodine atom, preferably, a fluorine or chlorine atom.

The perfluoroalkyl compounds having the formula (I) of the present invention can be prepared by the following reaction scheme:

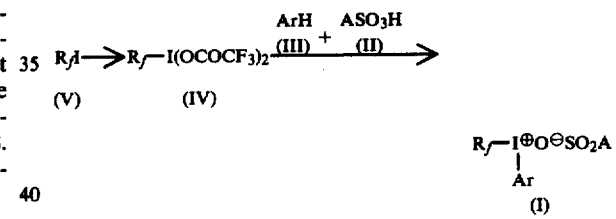

wherein $R_f$, I, Ar and A are as defined above.

The process according to the present invention comprises reacting an iodoperfluoroalkane of the formula (V)

(V)

wherein $R_f$ is as defined above, with an aqueous hydrogen peroxide solution having a hydrogen peroxide concentration of 40% or less and trifluoroacetic anhydride to produce a perfluoroalkyliodo compound of the formula (IV)

(IV)

wherein $R_f$ is as defined above, and reacting the perfluoroalkyliodo compound of the formula (IV) with a substituted or unsubstituted benzene of the formula (III)

(III)

wherein Ar is as defined above, and a sulfonic acid of the formula (II)

(II)

wherein A is as defined above.

The starting material, iodoperfluoroalkanes (V), are known compounds and can be easily available as commercial products.

In alternative procedures, the perfluoroalkyliodo compounds of the formula (IV) can be prepared by reacting an iodoperfluoroalkane (V) using hydrogen peroxide of 75% or more, as described in Zh. Organ. Khim., 6, 329 (1970); oxidizing an iodoperfluoroalkane (V) with ozone and then treating with trifluoroacetic anhydride; or fluorinating an iodoperfluoroalkane (V) and then treating the fluorinated compound with trifluoroacetic acid, as described in J. Fluorin Chem., 8, 177 (1976).

Examples of perfluoroalkyliodo compounds of the formula (IV) are di(trifluoroacetoxy)iodotrifluoromethane [$CF_3I(OCOCF_3)_2$], di(trifluoroacetoxy)iodopentafluoroethane [$C_2H_5I(OCOCF_3)_2$], di(trifluoroacetoxy)iodoheptafluoro-n-propane [$n-C_3F_7I(OCOCF_3)_2$], di(trifluoroacetoxy)iodoheptafluoro-i-propane [$i-C_3F_7I(OCOCF_3)_2$], di(trifluoroacetoxy)iodoperfluorohexane [$C_6F_{13}I(OCOCF_3)_2$], di(trifluoroacetoxy)iodoperfluorooctane [$C_8F_{17}I(OCOCF_3)_2$], di(trifluoroacetoxy)iodoperfluorodecane [$C_{10}F_{21}I(OCOCF_3)_2$] and the like.

Examples of substituted or unsubstituted benzene of the formula (III) are benzene, alkylbenzenes having 1 to 4 carbon atoms in the alkyl moiety such as toluene, halogenated benzenes such as fluorobenzene and the like. These substituted or unsubstituted benzenes are commercially available.

Examples of sulfonic acids of the formula (II) are sulfuric acid, halosulfonic acids such as fluorosulfonic acid, chlorosulfonic acid and the like, alkanesulfonic acids such as methanesulfonic acid, ethanesulfonic acid, butanesulfonic acid and the like, arylsulfonic acids such as benzenesulfonic acid, toluenesulfonic acid, nitrobenzenesulfonic acid, halonitrobenzenesulfonic acids and the like, perfluoroalkanesulfonic acid such as trifluoromethanesulfonic acid, perfluorobutanesulfonic acid, perfluorohexanesulfonic acid, perfluorooctanesulfonic acid and the like. These sulfonic acids are also easily available as commercial products.

The reaction between the iodoperfluoroalkane of the formula (V), the aqueous hydrogen peroxide solution and trifluoroacetic anhydride can be carried out at a temperature of about −50° C. to about 100° C., preferably −15° C. to room temperature (about 15°–30° C.), for a period of about 1 to about 24 hours. The aqueous hydrogen peroxide solution having a hydrogen peroxide concentration of 40% or less can be used in an amount of 1 to 4 mols per mol of the iodoperfluoroalkane of the formula (V). The trifluoroacetic anhydride can be used in an amount of an approximately equimolar amount or more to the total mols of hydrogen peroxide and water contained in the aqueous hydrogen peroxide solution.

The reaction between the perfluoroiodo compound of the formula (IV) obtained as above and the substituted or unsubstituted benzene of the formula (III) and the sulfonic acid of the formula (II) can be achieved by mixing these reactants together. In carrying out the reaction, a solvent is preferably used and examples of solvents are carboxylic acids such as trifluoroacetic acid and the like, acid anhydrides such as trifluoroacetic anhydride and the like, halogen-containing compounds such as dichloromethane, chloroform and the like. These solvents can be used alone or as a mixture thereof. The reaction proceeds at a temperature from about −100° C. to about 50° C., but is preferably conducted at 0° C. to room temperature (about 15°–30° C.).

The resulting compound of the formula (I) can be isolated from the reaction mixture in a conventional manner such as filtration, crystallization, etc. and can be purified by, for example, recrystallization, etc.

Typical examples of the perfluoroalkyl compounds of the formula (I) are as follows:

pentafluoroethylphenyliodonium trifluoromethanesulfonate, pentafluoro-n-propylphenyliodonium trifluoromethanesulfonate, pentafluoro-i-propylphenyliodonium trifluoromethanesulfonate, perfluoro-n-hexylphenyliodonium trifluoromethanesulfonate, perfluoro-n-heptylphenyliodonium trifluoromethanesulfonate, perfluoro-n-octylphenyliodonium trifluoromethanesulfonate, perfluoro-n-decylphenyliodonium trifluoromethanesulfonate, trifluoromethylphenyliodonium trifluoromethanesulfonate, perfluoro-n-octylphenyliodonium methanesulfonate, heptafluoro-n-propyl-p-tolyliodonium methanesulfonate, mono(pentafluoroethylphenyliodonium) sulfate, mono(heptafluoro-n-propylphenyliodonium) sulfate, mono(perfluoro-n-hexylphenyliodonium) sulfate, mono(perfluoro-n-octylphenyliodonium) sulfate, mono(perfluoro-n-decylphenyliodonium) sulfate, pentafluoroethylphenyliodonium fluorosulfate, heptafluoro-n-propyl-p-tolyliodonium benzenesulfonate, and the like.

Also, in an alternative procedure, the perfluoroalkyl compounds of the formula (I) can be prepared according to the following reaction scheme:

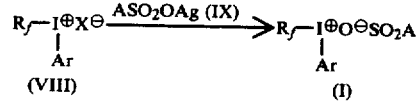

wherein X represents a halogen atom and $R_f$, Ar and A are as defined above.

The above alternative process for preparing the perfluoroalkyl compounds of the formula (I) comprises reacting an iodonium halide compound of the formula (VIII) with a silver sulfonate of the formula (IX). The reaction between the compounds of the formulae (VIII) and (IX) can be carried out in a polar solvent such as acetonitrile or ether solvents at a temperature of about −50° C. to about 50° C., preferably 0° C. to room temperature, as illustrated in Examples 11 and 12 hereinafter described.

As set forth above, the perfluoroalkylthio compounds represented by the formula (VI)

wherein $R_f$ is as defined above and R represents an unsubstituted or substituted alkyl group, which can be prepared by reacting the perfluoroalkyl compound of the formula (I) with a mercapto compound of the formula (VII)

HS—R  (VII)

wherein R is as defined above, are useful as chemical modifying agents. For example, pentafluoroethylthioacetic acid obtained in Reference Example 6 can be used as a chemical modifying agent for cephalosporin to produce 7-pentafluoroethylthioacetamido-3-(1-methyl-1H-tetrazol-5-yl)thiomethyl-3-cephem-4-carboxylic acid having the following antimicrobial activities:

| Test Organism | Minimum Inhibitory Concentration ($\mu$g/ml) |
|---|---|
| Staphylococcus aureus 209-P | 0.4 |
| Staphylococcus aureus Smith | 3.12 |
| Staphylococcus epidermidis | 6.25 |
| Escherichia coli NIHJC-2 | 25 |
| Escherichia coli GN2411-5 | 12.5 |
| Klebsiella pneumoniae 8045 | 6.25 |
| Proteus mirabilis 1287 | 12.5 |
| Pseudomonas putida 264 | 25 |
| Escherichia coli S 1073 | 12.5 |
| Escherichia coli S 1049 | 12.5 |
| Escherichia coli Rms 213 S 1113* | 25 |

*Penicillinase-producing bacteria

The present invention is further illustrated in greater detail by the following Examples and Reference Examples, but they are not to be construed as limiting the present invention.

EXAMPLE 1

To a mixture of 18.6 ml (132 mmols) of trifluoroacetic anhydride and 32 ml of trifluoroacetic acid was added dropwise 1.66 ml of a 30% aqueous hydrogen peroxide solution ($H_2O_2$, 16.3 mmols and $H_2O$, 71.7 mmols) in an ice bath. After completion of the addition, the mixture was stirred for 3 hours and 0.90 ml (8.13 mmols) of pentafluoroethyl iodide was added thereto, followed by allowing the mixture to react at 0° to 5° C. for 24 hours. The solvent was then distilled off to obtain 3.3 g (85% yield) of di(trifluoroacetoxy)iodopentafluoroethane as a white fluffy crystals.

Decomposition Point: 27°–28° C.

IR (KBr): 1680, 1430, 1320, 1210, 1130, 840, 800, 720 cm$^{-1}$

EXAMPLE 2

The same procedure as described in Example 1 was followed using the same molar ratio of the reagent except that 0.97 ml (6.76 mmols) of heptafluoro-n-propyl iodide was used instead of pentafluoroethyl iodide and 3.5 g (98% yield) of di(trifluoroacetoxy)iodopentafluoro-n-propane was obtained as white fluffy crystals.

Decomposition Point: 57°–61° C.

IR (KBr): 1680, 1430, 1320, 1210, 1130, 840, 800, 720 cm$^{-1}$

EXAMPLE 3

The same procedure as described in Example 1 was followed using the same molar ratio of the reagent except that 2.0 g (4.5 mmols) of tridecafluoro-n-hexyl iodide was used instead of pentafluoroethyl iodide and 2.6 g (85% yield) of di(trifluoroacetoxy)iodotridecafluoro-n-hexane was obtained as white fluffy crystals.

Melting Point: 60°–62° C.

IR (KBr): 1680, 1430, 1210, 1120, 830, 800, 720 cm$^{-1}$

EXAMPLE 4

The same procedure as described in Example 1 was followed using the same molar ratio of the reagent except that 2.0 g (4.0 mmols) of pentadecafluoro-n-heptyl iodide was used instead of pentafluoroethyl iodide and 2.6 g (91% yield) of di(trifluoroacetoxy)iodopentadecafluoro-n-heptane was obtained as white fluffy crystals.

Melting Point: 68°–70° C.

IR (KBr): 1680, 1430, 1200, 1120, 830, 800, 720 cm$^{-1}$

EXAMPLE 5

The same procedure as described in Example 1 was followed using the same molar ratio of the reagent except that 2.0 g (3.7 mmols) of heptadecafluoro-n-octyl iodide was used instead of pentafluoroethyl iodide and 2.6 g (92% yield) of di(trifluoroacetoxy)iodoheptadecafluoro-n-octane was obtained as white fluffy crystals.

Melting Point: 70°–74° C.

IR (KBr): 1680, 1430, 1200, 1120, 830, 800, 720 cm$^{-1}$

EXAMPLE 6

1.3 ml (9.3 mmols) of trifluoroacetic anhydride was dissolved in 3.3 ml of trifluoroacetic acid, and 0.175 ml of a 30% hydrogen peroxide solution ($H_2O_2$, 1.71 mmol and $H_2O$, 7.55 mmols) was added dropwise thereto while cooling in an ice bath. After completion of the addition, the mixture was stirred for 1.5 hour and 1.55 mmol of heptadecafluoro-n-octyl iodide was added and the mixture was allowed to react at 0° to 5° C. for 18 hours to obtain di(trifluoroacetoxy)iodoheptadecafluoro-n-octane in 66% yield.

EXAMPLE 7

To a mixture of 10.6 ml (75.2 mmols) of trifluoroacetic anhydride and 30 ml of trifluoroacetic acid was added dropwise 1.36 ml of a 35% aqueous hydrogen peroxide solution ($H_2O_2$, 15.7 mmols and $H_2O$, 55 mmols) in an ice bath. After completion of addition, the mixture was stirred for 1.5 hour and 5.0 g (7.7 mmols) of heneicosafluoro-n-decyl iodide was added thereto, followed by allowing the mixture to react at 0° to 5° C. for 24 hours. The solvent was then distilled off to obtain 6.3 g (94% yield) of di(trifluoroacetoxy)iodoheneicosafluoro-n-decane as white fluffy crystals.

Melting Point: 83°–88° C.

IR (KBr): 1680, 1430, 1200, 1140, 830, 800, 720 cm$^{-1}$

Elementary Analysis: Found: C, 19.39; Calc'd: C, 19.28

EXAMPLE 8

The same procedure as described in Example 6 was followed except that heneicosafluoro-n-decane was used instead of heptadecafluoro-n-octane and di(trifluoroacetoxy)iodoheneicosafluoro-n-decane was obtained in 81% yield.

EXAMPLE 9

To a mixture of 6.05 g of di(trifluoroacetoxy)iodopentafluoroethane and 45 ml of trifluoroacetic acid was added 1.1 ml of trifluoromethanesulfonic acid while cooling in an ice bath and stirring, and thereafter 1.2 ml of benzene was added dropwise to the mixture. After completion of the addition, the mixture was stirred for 4.5 hours and the solvent was distilled off to obtain a crystalline solid which was then recrystallized from chloroform to obtain 3.32 g (55% yield) of pentafluoroethylphenyliodonium trifluoromethanesulfonate as colorless flake crystals.

Decomposition Point: 116°–120° C.

19F-NMR (CCl3F internal standard in CDCl3): 76.03 ppm (q, J=4Hz, —CF2—), 78.93 (s, CF3SO2—), 80.94 (t, J=4Hz, —CF2—CF3).

1H-NMR (in CDCl3): 7.4–8.2 ppm (m, 5H).

IR (nujol): 3400, 1460, 1440, 1315, 1280, 1220, 1380, 1310, 1020, 980, 895, 740, 675, 640, 570, 520 cm$^{-1}$.

Elementary Analysis: Found: C, 22,62;H, 1.07%; Calc'd: C, 22,90;H, 1.07%

EXAMPLE 10

To a mixture of 7.0 ml of trifluoroacetic acid and 1.0 g of di(trifluoroacetoxy)iodopentafluoroethane was added 0.12 ml of concentrated sulfuric acid while cooling in an ice bath with stirring, and 0.28 ml of benzene was added dropwise to the mixture. After completion of the addition, the mixture was stirred for 3 hours, allowed to warm to room temperature and the solvent was distilled off to obtain a crystalline solid which was then recrystallized from chloroform to obtain 645 mg (72.5% yield) of mono(pentafluoroethylphenyliodonium)sulfate as colorless crystals.

Melting Point: 107°–108° C.

19F-NMR (CCl3F internal standard in CD3OH): -79.81 ppm (q, $J_{CF_2, CF_3}$=4 Hz, CF2), -80.87 ppm (t, $J_{CF_2, CF_3}$=4 Hz, CF3).

1H-NMR (in CD3CO): 7.58–8.03 ppm (multi, m-H, p-H, 3H), 8.37 ppm (d, $J_{O-H, m-H}$=7.5 Hz, O-H, 2H).

IR (nujol)- 3080, 2450, 2350, 1580, 1460, 1320, 1220, 1215, 1195, 1140, 1100, 1040, 1005, 980, 895, 880, 845, 745, 740, 675, 650, 620, 600, 570, 540 cm$^{-1}$

MS: 322

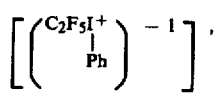

254, 204 (PHI$^+$), 119 (C2$^+$F5), 77 (PH$^+$), 69 (C$^+$F3).

Elementary Analysis: Calc'd: C, 22.87; H, 1.44% Found: C, 22.92; H, 1.41%

EXAMPLE 11

To a mixture of 5.0 g of di(trifluoroacetoxy)iodoheptafluoro-n-propane and 50 ml of trifluoroacetic acid was added 1.3 ml of benzene while cooling in an ice bath with stirring and, thereafter, 0.85 ml of trifluoromethanesulfonic acid was added dropwise thereto. After stirring the mixture for 3 hours, the mixture was allowed to warm to room temperature, and the solvent was distilled off. The residue was extracted with chloroform and the extract was filtered and concentrated. Upon allowing to stand, 3.4 g (68% yield) of heptafluoro-n-propylphenyliodonium trifluoromethanesulfonate was obtained as colorless plate crystals.

Decomposition Point: 124.5°–127° C.

19F-NMR (CCl3F internal standard in CDCl3): 70.65 ppm (b.s, —CF2—I), 79.00 (s, —SO2CF3), 79.70 (t, J=8 Hz, CF3—CF2—), 118.5 (s, CF3—CF2—).

1H-NMR (in CDCl3): 7.4–8.2 ppm (m, 5H).

IR (nujol): 3090, 1460, 1445, 1320, 1275, 1240, 1220, 1195, 1165, 1135, 1055, 1015, 980, 800, 740, 725, 675, 635, 520 cm$^{-1}$ Elementary Analysis: Found: C, 22.94; H, 0.93%; Calc'd: C, 23.01; H, 0.97%

EXAMPLE 12

The same procedure as described in Example 10 was followed to prepare mono(heptafluoro-n-propylphenyliodonium) sulfate. Yield, 44%.

Melting Point: 109°–111° C.

19F-NMR (CCl3F internal standard in CD3CN): -75.65 ppm (q, $J_{CF_2,CF_3}$=10 Hz; αCF2), -78.94 ppm (t, $J_{CF_3,CF_2}$=10 Hz, CF3), -118.1 ppm (s, β-CF2).

1H-NMR (in CDCL3): 7.4–7.9 ppm (multi, n-H, p-H, 3H), 8.2 ppm (d, $J_{O-H, m-H}$=9 Hz, OH, 2H).

IR (nujol): 1330, 1280, 1210, 1140, 1060, 1040, 1020, 985, 880, 810, 750, 730, 680, 650, 580 cm$^{-1}$ MS: 375 [(C3F7—I$^+$—Ph)-1], 253, 204, 69.

Elementary Analysis: Found: C, 23.04; H, 1.34%; Calc'd: C, 23.00; H, 1.29%

EXAMPLE 13

0.24 g of silver methanesulfonate and 7 ml of acetonitrile were charged in a flask substituted with argon, and a solution of 0.5 g of heptafluoro-n-propyl-p-tolyliodonium chloride dissolved in 8 ml of acetonitrile was added dropwise thereto while cooling in an ice bath with stirring. After completion of the addition, the mixture was stirred for one hour while cooling in an ice bath, and the precipitated white crystals were removed by filtration. The solvent was then removed from the filtrate to obtain white crystals which were then recrystallized from methylene chloride-pentane to obtain 0.35 g (61.4% yield) of heptafluoro-n-propyltolyliodonium methanesulfonate.

Melting Point: 117.5°–119° C.

19F-NMR (CCl3F internal standard in CDCl3): -78.05 ppm (q, $J_{CF_2,CF_3}$=8.0 Hz, α-CF2)3, -79.74 ppm (t, $J_{CF_2,CF_3}$=8.0 Hz, CF3), -119.3 ppm (br. s, β-CF2).

1H-NMR (in CDCl3): 2.55 ppm (s, Ar—CH3), 2.68 ppm (s, OSO2CH3), 7.52 ppm (d, J=9 Hz, ArH, 2H), 8.22 ppm (d, J=9 Hz, ArH, 2H).

IR (nujol): 3070, 1460, 1400, 1380, 1325, 1275, 1225, 1205, 1200, 1180, 1150, 1130, 1060, 1050, 1020, 860, 800, 880, 865, 830, 670, 620, 585, 575, 550, 535, 490 cm$^{-1}$

MS: 386

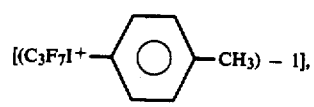

267, 218, 91.

Elenentary Analysis: Found: C, 27.41; H, 2.15%; Calc'd: C, 27.40; H, 2.09%

EXAMPLE 14

0.31 g of silver benzenesulfonate and 5 ml of acetonitrile were charged in a flask substituted with argon, and a solution of 0.5 g of heptafluoro-n-propyl-p-tolyliodonium chloride dissolved in 7 ml of acetonitrile was added dropwise thereto while cooling in an ice bath with stirring. After completion of addition, the mixture was stirred for one hour while cooling in an ice bath, and the precipitated white crystals were removed by filtration. The solvent was then removed from the filtrate to obtain white crystals which were then recrystallized from methylene chloride-pentane to obtain 0.42 g (66% yield) of heptafluoro-n-propyl-p-tolyliodonium benzenesulfonate.

Melting Point: 128°–130° C.

$^{19}$F-NMR (CCl$_3$F internal standard in CDCl$_3$): -78.38 ppm (q, J$_{CF_2,CF_3}$=8.0 Hz, α-CF$_2$), -79.79 ppm (t, J$_{CF_2,CF_3}$=8.0 Hz, CF$_3$), -119.3 ppm (s, CF$_2$).

$^1$H-NMR (CDCl$_3$): 2.40 ppm (s, -CH$_3$), 7.24 ppm (multi, OSO$_2$Ph), 7.54 ppm (br. d, J=8.0 Hz, ArH, 2H), 7.95 ppm (d, J=8.0 Hz, ArH, 2H).

IR (nujol); 3090, 3050, 1480, 1460, 1450, 1380, 1330, 1280, 1235, 1210, 1195, 1180, 1160, 1130, 1120, 1065, 1030, 1010, 995, 810, 755, 730, 690, 670, 610, 560, 490 cm$^{-1}$

MS: 386

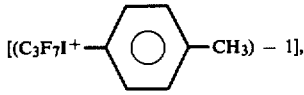

267, 218, 91

Elementary Analysis: Found: C, 35.21; H, 2.17%; Calc'd: C, 35.31; H, 2.22%

EXAMPLE 15

0.93 g of di(trifluoroacetoxy)iodoheptafluoro-n-propane and 7 ml of trifluoroacetic acid were charged in a flask and, after addition of 0.24 ml of benzene, 0.102 ml of fluorosulfonic acid was added dropwise thereto while cooling in an ice bath, followed by stirring the mixture while cooling in an ice bath for 2 hours. The mixture was then stirred at room temperature for one hour and the solvent was distilled off to obtain heptafluoro-n-propylphenyliodonium fluorosulfonate.

$^{19}$F-NMR (CCl$_3$F internal standard in chloroform): 38.52 ppm (br. s, OSO$_2$F), -69.00 ppm (br. s, α-CF$_2$), -79.74 ppm (t, J$_{CF_3,CF_2}$=8 Hz, γ-CF$_3$), -118.4 ppm (s, β-CF$_2$).

The product was confirmed by converting into mono(heptafluoro-n-propylphenyliodonium) sulfate after hydrolyzing the product with acetonitrile in the air followed by crystallization.

EXAMPLE 16

0.2 ml of benzene was added to a mixture of 1.0 g of di(trifluoroacetoxy)iodoperfluoro-n-hexane and 10 ml of trifluoroacetic acid while cooling in an ice bath, and then 0.13 ml of trifluoromethanesulfonic acid was added dropwise thereto with stirring. After stirring for 2.5 hours, the solvent was distilled off and the resulting solid was recrytallized from chloroform to obtain 0.82 g of perfluoro-n-hexylphenyliodonium trifluoromethanesulfonate as colorless needles. Yield, 82%.

Decomposition Point: 120°-123° C.

$^{19}$F-NMR (CCl$_3$F internal standard in CDCl$_3$); 70.35 ppm (m, 2F), 79.00 (s, 3F), 81.28 (t, 3F), 114.2 (m, 2F), 121.7 (m, 2F), 123.0 (m, 2F), 126.5 (m, 2F).

$^1$H-NMR (in CDCl$_3$): 7.4-8.4 ppm (m, 5H).

IR (nujol): 1360, 1340, 1240, 1020, 735, 640 cm$^{-1}$

EXAMPLE 17

The same procedure as described in Example 10 was followed except that di(trifluoroacetoxy)iodotridecafluoro-n-hexane was used instead of di(trifluoroacetoxy)iodopentafluoroethane to obtain mono(tridecafluoro-n-hexylphenyliodonium) sulfate. Yield, 51%.

Melting Point: 107°-108° C.

$^{19}$F-NMR (CCl$_3$F internal standard in CD$_3$CN): -73.35 ppm (t, J=12 Hz, α-CF$_2$), -80.26 ppm (t, J=10 Hz, CF$_3$), -113.3 ppm (m, CF$_2$), -120.5 ppm (m, CF$_2$), -121.7 ppm (m, CF$_2$), -125.2 ppm (m, CF$_2$).

$^1$H-NMR (in CD$_3$CN): 7.5-8.0 ppm (multi, m-H, p-H, 3H), 8.3 ppm (d, J$_{O-H, m-H}$=9 Hz, o-H, 2H).

IR (nujol): 3350, 3070, 1460, 1450, 1380, 1360, 1310, 1280, 1240, 1215, 1195, 1190, 1140, 1120, 1095, 1060, 1020, 985, 880, 850, 750, 740, 720, 680, 660, 645, 590, 580, 530 cm$^{-1}$ MS: 522 [(C$_6$F$_{13}$I+Ph)-1], 253, 204.

Elementary Analysis: Found: C, 23.20; H, 1.06%; Calc'd: C, 23.24; H, 0.98%

EXAMPLE 18

0.18 ml of benzene was added to a mixture of 1.0 g of di(trifluoroacetoxy)iodoperfluoro-n-heptane and 15 ml of trifluoroacetic acid while coolig in an ice bath, and then 0.12 ml of trifluoromethanesulfonic acid was added dropwise thereto with stirring. After stirring for 2.5 hours, the solvent was distilled off and the resulting residue was recrystallized from chloroform to obtain 0.75 g of perfluoro-n-heptylphenyliodonium trifluoromethanesulfonate as colorless fine needles. Yield, 75%.

Decomposition Point: 148°-150° C. $^{19}$F-NMR (CCl$_3$F internal standard in acetone-d$_6$): 71.41 ppm (t, 2F), 78.07 (s, 3F), 80.59 (t, 3F), 113.3 (m, 2F), 121.0 (m, 4F), 122.1 (m, 2F), 125.6 (m, 2F).

$^1$H-NMR (in acetone-d$_6$): 8.0 ppm (m, 3H), 8.7 ppm (m, 2H).

IR (nujol): 1383, 1280, 1240, 1220, 1150, 1020, 745, 640 cm$^{-1}$

Elementary Analysis: Found: C, 23.26; H, 0.61%; Calc'd: C, 23.29; H, 0.70%

EXAMPLE 19

0.86 ml of benzene was added to a mixture of 5 g of di(trifluoroacetoxy)iodoperfluoro-n-octane and 30 ml of trifluoroacetic acid while cooling in an ice bath, and then 0.57 ml of trifluoromethanesulfonic acid was added dropwise thereto with stirring. After stirring for 3 hours, the solvent was distilled off and the resulting solid was recrystallized from chloroform to obtain 3.93 g of perfluoro-n-octylphenyliodonium trifluoromethanesulfonate as colorless fine needles. Yield, 79%.

Decomposition Point: 149°-151° C.

$^{19}$F-NMR (CCl$_3$F internal standard in acetone-d$_6$): 71.34 ppm (t, 2F), 78.17 (s, 3F), 80.65 (t, 3F), 113.3 (m, 2F), 121.0 (m, 6F, 122.1 (m, 2F), 125.7 (m, 2F).

$^1$H-NMR (in acetone-d$_6$): 8.0 ppm (m, 3 H), 8.7 (m, 2H).

IR (nujol): 1360, 1350, 1240, 1020, 740, 640 cm$^{-1}$

Elementary Analysis: Found: C, 23.28; H, 0.59%; Calc'd: C, 23.33; H, 0.65%

EXAMPLE 20

The same procedure as described in Example 10 was followed to prepare mono(n-perfluorooctylphenyliodonium) sulfonate monohydrate. Yield, 62%.

Melting Point: 114°-118° C.

$^{19}$F-NMR (CCl$_3$F internal standard in CD$_3$CN): -72.69 ppm (multi, α-CF$_2$), -80.20 ppm (t, J=10 Hz, CF$_3$), -113.1 ppm (multi, CF$_2$), -120.6 ppm (multi, CF$_2$×3), -121.7 ppm (multi, CF$_2$), -125.1 ppm (multi, CF$_2$).

$^1$H-NMR (in CD$_3$CN): 7.5-8.0 ppm (m-H, p-H, 3 H), 8.3 ppm (d, J$_{o-H, m-H}$=9 Hz, o-H, 2H).

IR (nujol): 3370, 1320, 1245, 1210, 1150, 1095, 1060, 1020, 980, 915, 880, 735, 640, 560, 530 cm$^{-1}$ MS: 611 (n-C$_8$F$_{17}$I+Ph—H), 253 (C+F$_2$IPh—H), 204 (PhI+), 60 (C+F$_3$).

EXAMPLE 21

1.0 g (1.30×10⁻³ mol) of di(trifluoroacetoxy)iodoheptadecafluoro-n-octane was suspended in 6.0 ml of trifluoroacetic acid, and 0.173 ml (1.95×10⁻³ mol) of benzene and then 0.0843 ml (1.30×10⁻³ mol) of methanesulfonic acid were added dropwise to the suspension, followed by allowing the mixture to react for 2 weeks at room temperature. The reaction mixture was dried up and a small amount of acetonitrile was added thereto to obtain 240 mg (26% yield) of heptadecafluoro-n-octylphenyliodonium methanesulfonate as white crystals. A sample of the resulting product was recrytallized from acetonitrile for elementary analysis and measurements of spectra. The data obtained are shown below. Melting Point: 140°–141° C.

$^{19}$F-NMR (CCl$_3$F internal standard in CDCl$_3$): -77.09 ppm (t, J$_{CF2,CF2}$=15 Hz, CF$_2$, 2F), -81.32 ppm (t, J$_{CF2,CF2}$=10 Hz, CF$_3$, 3F), -114.82 ppm (m, CF$_2$, 2F), -122.01 ppm (m, CF$_2$×3, 6F), -123.04 ppm (m, CF$_2$ 2F), -126.52 ppm (m, CF$_2$, 2F).

$^1$H-NMR (in CDCl$_3$): 2.50 ppm (s, 3H), 7.70 ppm (m, 3H), 8.24 ppm (m, 2H).

IR (KBr): 3050, 1465, 1440, 1365, 1320, 1200 (broad absorption). 1140, 1085, 1055, 1025, 980, 900, 810, 780, 770, 740, 730, 635, 555, 530 cm⁻¹

MS: 523 (C$_8$F$_{17}$I+Ph), 622 [(C$_8$F$_{17}$I+Ph)-1], 254, 253, 204.

Elementary Analysis: Found: C, 25.09; H, 1.04% Calc'd: C, 25.09; H, 1.12%

EXAMPLE 22

0.92 ml (10 mmol) of benzene was added to a mixture of 6.0 g (6.9 mmol) of di(trifluoroacetoxy)iodoheneicosafluoro-n-decane and 32 ml of trifluoroacetic acid under cooling in an ice bath with stirring, and then 0.61 ml (6.9 mmol) of trifluoromethanesulfonic acid was added dropwise thereto. After completion of the addition, the mixture was stirred for 1.5 hours and the solvent was distilled off to obtain a crystalline solid. The solid was washed with hot chloroform to obtain 4.4 g of heneicosafluoro-n-decylphenyliodonium trifluoromethanesulfonate. Yield, 73%. Melting Point 162°–166° C.

$^{19}$F-NMR (CCl$_3$F intfernal standard in CD$_3$CN): 67.44 ppm (t, J=10 Hz, —CF$_2$I), 78.18 ppm (s, —SO$_2$CF$_3$), 80.27 ppm (t, J=10 Hz, CF$_3$—), 112.8 ppm-125.3 ppm (-(-CF$_2$-)$_8$)

IR (KRb): 1460, 1440, 1370, 1330, 1210, 1140, 1080, 1020, 980, 940, 820, 740, 730, 630, 540, 520 cm⁻¹

Elementary Analysis: Found: C, 23.49; H, 0.57%; Calc'd: C, 23.41; H, 0.58%

EXAMPLE 23

The same procedure as described in Example 10 was followed using the same molar ratio of the reagent except that di(trifluoroacetoxy)iodoheneicosafluoro-n-decane was used instead of di(trifluoroacetoxy)iodoheptadecafluoro-n-octane and 2.3 g (81% yield) of mono(heneicosafluoro-n-decylphenyliodo)sulfonate monohydrate was obtained.

Melting Point: 129°–132° C.

$^{19}$F-NMR (CCl$_3$F internal standard in CD$_3$CN): -73.27 ppm (t, -CF$_2$.I), -80.15 ppm (t, CF$_3$—), -113.25~-125.14 ppm [-(-CF$_2$.CF$_2$-)$_4$].

IR (KBr): 1460, 1440, 1380, 1210, 1150, 1120, 1090, 1070, 1040, 1010, 990, 890, 850, 830, 740, 640, 580, 560, 530 cm⁻¹

Elementary Analysis: Found: C, 23.00; H, 0.92%; Calc'd: C, 22.93; H, 0.96%

REFERENCE EXAMPLE 1

A mixture of 0.5 g of 2(1H), 3(4H)-quinoxalinedione, 1.60 g of pentafluoroethylphenyliodonium trifluoromethanesulfonate and 10 ml of dimethylformamide was stirred overnight on an oil bath at 45° C. Ethyl acetate was then added to the reaction mixture and the unreacted 2(1H), 3(4H)-quinoxalinedione was removed by filtration (recovery of the starting material: 0.13 g). Water was added to the filtrate and, after rendering the mixture neutral, the mixture was extracted with ethyl acetate. The extract was washed with water, dried over magnesium sulfate, and the solvent was distilled off. A small amount of methylene chloride was added to the residue and the precipitated crystals were collected by filtration to obtain 0.05 g of 6-pentafluoroethyl-2(1H), 3(4H)-quinoxalinedione as colorless crystals. Yield 6% (conversion yield, 8%). Melting Point (after recrystallized from acetonitrile): 317°–320° C. (with decomposition).

$^{19}$F-NMR (CCl$_3$F internal standard, acetone-d$_6$): 84.40 ppm (t, J=2 Hz, CF$_3$), 113.1 (q, J=2 Hz, CF$_2$)

$^1$H-NMR (acetone-d$_6$): 7.50 ppm (b.s, 2H, aromatic hydrogen), 7.60(b.s, 1H, aromatic hydrogen), 11.1 (b.s, 2H, hydroxy hydrogen)

IR (nujol): 3250, 3170, 1725, 1700, 1620, 1400, 1305, 1210, 1180, 1135, 1100, 1050, 930, 820, 775, 740, 675, 650 cm⁻¹

MS (m/e): 280 (M+)

Elementary Analysis: Found: C, 42.96; H, 1.84; N, 10.07%; Calc'd: C, 42.87; H, 1.80; N, 10.00%

REFERENCE EXAMPLE 2

0.08 g of sodium hydride (50% in oil) was added to 3.5 ml of dried dimethyl sulfoxide and the mixture was stirred for 25 minutes on an oil bath at 65° C. in an argon atmosphere. Thereafter, 0.25 g of 2(1H), 3(4H)-quinoxaline was added thereto and the mixture was stirred for 30 minutes. After allowing to cool to room temperature, 0.80 g of pentafluoroethylphenyliodonium trifluoromethanesulfonate was added to the mixture. At this time, an exothermic reaction occurred and the mixture was cooled with ice-water. The mixture was then stirred overnight at room temperature and, after adding water thereto, the mixture was extracted with ethyl acetate. The extract was dried over magnesium sulfate and the solvent was distilled off. To the resulting residue was added a small amount of methylene chloride and the precipitated crystals were collected by filtration to obtain 0.16 g of 6-pentafluoroethyl-2(1H), 3(4H)-quinoxalinedione as colorless crystals. From the aqueous phase, 0.06 g of the unreacted starting material (2(1H), 3(4H)-quinoxalinedione) was recovered. Yield 37% (conversion yield, 49%).

REFERENCE EXAMPLE 3

2.0 ml of methylene chloride, 0.06 ml (0.68 mmol) of 2-mercaptopropionic acid and 140 mg (0.68 mmol) of 2,6-di-tert-butyl-4-methylpyridine were charged in a flask, and 320 mg (0.68 mmol) of pentafluoroethylphenyliodonium trifluoromethanesulfonate was added thereto in small portions while stirring at room temperature, followed by stirring the mixture at room temperature for 20 minutes. The resulting precipitate was filtered, subjected to column chromatography of silica gel and, after eluting iodobenzene with pentane, the desired product was eluted with diethyl ether. Diethyl ether was distilled off from the eluate to obtain 2-pentafluoroethylthiopropionic acid as a colorless liquid. A sample of the product was purified by gas chromatography. Yield, 81%.

$^{19}$F-NMR (CCl$_3$F internal standard in CDCl$_3$): -84.02 ppm (t, $J_{CF_3,CF_2}$=3.5 Hz, CF$_3$, 3F), -91.67 ppm (q, $J_{CF_3,CF_2}$=3.5 Hz, CF$_2$, 2F), $^1$H-NMR (in CDCl$_3$): 1.70 ppm (d, $J_{CH_3,CH}$=7.5 Hz, CH$_3$, 3H), 4.10 ppm (q, $J_{CH_3,CH}$=7.5 Hz, —SCH—, 1H), 10.53 ppm (s, CO$_2$H, 1H).

IR (neat): 3050 (broad absorption), 1730, 1460, 1415, 1380, 1320, 1280, 1210, 1100, 965, 750 cm$^{-1}$

MS: 224 (M+), 179, 69, 61, 62, 47, 45

Elementary Analysis: Found: C, 26.83; H, 2.29%; Calc'd: C, 26.79; H, 2.25%

REFERENCE EXAMPLE 4

2.0 ml of methylene chloride, 0.05 ml (0.58 mmol) of 3-mercaptopropionic acid and 120 mg (0.59 mmol) of 2,6-di-tert-butyl-4-methylpyridine were charged in a flask, and 261 mg (0.55 mmol) of pentafluoroethylphenyliodonium trifluoromethanesulfonate was added thereto in small portions while stirring at room temperature, followed by stirring the mixture at room temperature for 20 minutes. The resulting white precipitate was filtered, subjected to column chromatography of a small amount of silica gel and, after eluting iodobenzene with hexane, the desired product was eluted with diethyl ether. Diethyl ether was distilled off from the eluate to obtain 3-pentafluoroethylthiopropionic acid as a colorless liquid. A sample of the product was purified by gas chromatography. Yield, 83%.

$^{19}$F-NMR (CCl$_3$F internal standard in CDCl$_3$): -84.00 ppm (t, $J_{CF_3,CF_2}$=3.5 Hz, CF$_3$, 3F), -92.82 ppm (q, $J_{CF_3,CF_2}$=3.5 Hz, CF$_2$, 2F)

$^1$H-NMR (in CDCl$_3$): 2.79 ppm (t, J=7.0 Hz, CH$_2$SC$_2$F$_5$, 2H), 3.15 ppm (t, J=7.0 Hz, —CH$_2$CO—, 2H), 10.6 ppm (br.s, CO$_2$H, 1H)

IR (neat): 3050 (broad absorption), 2670, 2480, 1720, 1430, 1330, 1215, 1100, 970, 920, 810, 750, 650, 625, 585, 555 cm$^{-1}$

MS: 224 (M+), 179, 105, 87, 69, 63, 59, 45

Elementary Analysis: Found: C, 26.83; H, 2.31%; Calc'd: C, 26.79; H, 2.25%

REFERENCE EXAMPLE 5

2.0 ml of methylene chloride, 0.10 ml (0.42 mmol) of 1-dodecanethiol and 87 mg (0.42 mmol) of 2,6-di-tert-butyl-4-methylpyridine were added to a flask, and 198 mg (0.42 mmol) of pentafluoroethylphenyliodonium trifluoromethanesulfonate was added thereto in small portions while stirring at room temperature, followed by stirring at room temperature for 20 minutes. The resulting white precipitate was filtered and subjected to column chromatography of silica gel. Iodobenzene and the product were eluted with pentane and purified by gas chromatography to obtain 1-pentafluoroethylthiododecane as an oily substance. Yield, 87%.

$^{19}$F-NMR (CCl$_3$F internal standard in CDCl$_3$): -84.01 ppm (t, $J_{CF_3,CF_2}$=3.5 Hz, CF$_3$, 3F), -92.69 ppm (q, $J_{CF_3,CF_2}$=3.5 Hz, CF$_2$, 2F)

$^1$H-NMR (in CDCl$_3$): 0.90 ppm (s, CH$_3$), 1.29 ppm (br.s, CH$_2$×9), 1.53 ppm (s, SCH$_2$CH$_2$—), 2.92 ppm (t, $J_{CH_2,CH_2}$=7 Hz, SCH$_2$)

IR (neat): 2950, 2925, 2850, 1460, 1375, 1335, 1320, 1210, 1200, 1120, 1090, 970, 750, 720, 640, 620, 545 cm$^{-1}$

MS: 201 (C$_{12}$H$_{25}$S+), 106, 97, 83, 69, 57, 55, 43, 41, 29, 27

Elementary Analysis: Found: C, 26.83; H, 2.31%; Calc'd: C, 26.79; H, 2.25%

REFERENCE EXAMPLE 6

0.12 ml of mercaptoacetic acid and 350 ml of 2,6-di-tert-butyl-4-methylpyridine were added to 4 ml of methylene chloride and the mixture was stirred at room temperature. Then, 800 mg of pentafluoroethylphenyliodonium trifluoromethanesulfonate was added thereto and the mixture was allowed to react for 30 minutes at room temperature. The reaction mixture was subjected to column chromatography of silica gel and, after eluting iodobenzene with hexane, the product was eluted with diethyl ether. The diethyl ether was distilled off to obtain 319 mg (90% yield) of pentafluoroethylthioacetic acid as an oily substance. $^{19}$F-NMR (CCl$_3$F internal standard in CDCl$_3$): -83.98 ppm (t, $J_{CF_3,CF_2}$=3.5 Hz, CF$_3$), -93.39 ppm (q, $J_{CF_3,CF_2}$=3.5 Hz, CF$_2$)

$^1$H-NMR (in CDCl$_3$): 3.82 ppm (s, CH$_2$), 6.7 ppm (br.s, COOH)

IR (neat): 3100 (broad absorption), 2670, 2550, 1725, 1410, 1320, 1300, 1280, 1210, 1130, 1100, 970, 900, 775, 750, 640, 620 cm$^{-1}$

MS: 210 (M+), 165, 119, 69, 47, 45

Elementary Analysis: Found: C, 22.89; H, 1.63%; Calc'd: C, 22.87; H, 1.44%

REFERENCE EXAMPLE 7

0.012 ml of mercaptoacetic acid and 0.027 ml of pyridine were added to 1.5 ml of methylene chloride. Then, 69.0 mg of mono(pentafluoroethylphenyliodonium)sulfate was added thereto, and the mixture was allowed to react at room temperature for 20 minutes to obtain pentafluoroethylthioacetic acid. Yield, 71%.

REFERENCE EXAMPLE 8

2.5 ml of methylene chloride, 0.072 ml (0.62 mmol) of benzylmercaptan and 126 mg (0.61 mmol) of 2,6-di-tert-butyl-4-methylpyridine were charged in a flask, and 320 mg (0.61 mmol) of heptafluoro-n-propylphenyliodonium trifluoromethanesulfonate was added thereto in small portions while stirring at room temperature, followed by stirring for 10 minutes at room temperature. The resulting white precipitate was filtered, subjected to column chromatography of silica gel and eluted with pentane. Pentane was distilled off from the eluate and the residue was purified by gas chromatography to obtain benzylperfluoro-n-propylthio ether as an oily substance. Yield, 76%.

$^{19}$F-NMR (CCl$_3$F internal standard in CDCl$_3$): -80.50 ppm (t, $J_{CF_3,\alpha\text{-}CF_2}$=9.3 Hz, CF$_3$, 3F), -88.84 ppm (m, $J_{CF_3,\alpha\text{-}CF_2}$=9.3 Hz, $J_{\alpha\text{-}CF_2,\beta\text{-}CF_2}$=4.0 Hz, $\alpha$-CF$_2$,2F), -124.6 ppm (t, $J_{\alpha\text{-}CF_2,\beta\text{-}CF_2}$=4.0 Hz, $\beta$-CF$_2$, 2F)

$^1$H-NMR (in CDCl$_3$): 4.25 ppm (s, —CH$_2$—, 2H), 7.50 ppm (s, Ar-H, 5H)

IR (neat): 3100, 3070, 3040, 2950, 1950, 1880, 1800, 1600, 1495, 1455, 1335, 1220, 1210, 1180, 1110, 1080, 1035, 925, 855, 840, 810, 770, 750, 740, 700, 695, 670, 650, 605, 560, 535, 520 cm$^{-1}$

MS: 292 (M+), 91, 77, 69, 65

Elementary Analysis: Found: C, 41.07; H, 2.40%; Calc'd: C, 41.10; H, 2.41%

REFERENCE EXAMPLE 9

2.0 ml of methylene chloride, 57 mg (0.38 mmol) of mercaptosuccinic acid and 79 mg (0.39 mmol) of 2,6-di-tert-butyl-4-methylpyridine were added to a flask, and 204.2 mg (0.39 mmol) of heptafluoro-n-propylphenyliodonium trifluoromethanesulfonate was added thereto while stirring at room temperature, followed by stirring at room temperature for one hour. The resulting precipitate was filtered and subjected to column chromatography of silica gel. Iodobenzene was eluted with pentane and diethyl ether was passed through the column. Diethyl ether was distilled off from the eluate to obtain 62.9 mg (yield, 52.1%) of heptafluoro-n-propylthiosuccinic acid as crystals.

$^{19}$F-NMR (CCl$_3$F internal standard in CDCl$_3$): -80.49 ppm (t, $J_{CF_2,CF_3}=9.5$ Hz, CF$_3$), -87.56 ppm (m, $J_{CF_3,CF_2}=9.5$ Hz, $J_{CF_2,CF_2}=3.5$ Hz, CF$_2$CF$_2$CF$_3$), -124.5 ppm (t, $J_{CF_2,CF_2}=3.5$ Hz, CF$_2$CF$_2$CF$_3$)

$^1$H-NMR (in CDCl$_3$): 3.10 ppm (d, $J_{CH,CH_2}=7$ Hz, CH$_2$), 4.22 ppm (t, $J_{CH,CH_2}=7$ Hz, CH)

A portion of heptafluoro-n-propylthiosuccinic acid obtained in the above reaction was esterified as follows.

Heptafluoro-n-propylthiosuccinic acid was dissolved in diethyl ether and a solution of diazomethane dissolved in diethyl ether was added dropwise thereto at room temperature with stirring until the reaction was completed. After distilling off the diethyl ether, the residue was purified by gas chromatography to obtain dimethyl heptafluoro-n-propylthiosuccinate as an oily substance.

$^{19}$F-NMR (CCl$_3$F internal standard in CDCl$_3$): -80.47 ppm (t, $J_{CF_2,CF_3}=9.0$ Hz, CF$_3$), -87.55 ppm (m, α-CF$_2$), -124.5 ppm (t, $J_{CF_2,CF_3}=4.0$ Hz, β-CF$_2$)

$^1$H-NMR (in CDCl$_3$):

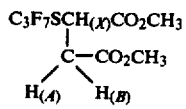

2.93 ppm (d.d., $J_{HA,HX}=5.8$ Hz, $J_{HA,HB}=17$ Hz, H$_A$, 1H), 3.09 ppm (d.d., $J_{HB,HX}=8.0$ Hz, $J_{HA,HB}=17$ Hz, H$_B$, 1H), 3.69 ppm (s, CH$_3$, 3H), 3.77 ppm (s, CH$_3$, 3 H), 4.23 ppm (d.d., $J_{HA,HX}=8.0$ Hz, $J_{HB,HX}=5.8$ Hz, H$_X$, 1H)

IR (neat): 3000, 2960, 2850, 1750, 1440, 1415, 1370, 1340, 1310, 1220, 1180, 1170, 1115, 1685, 1040, 1000, 960, 925, 905, 860, 810, 750, 745, 680, 540 cm$^{-1}$

MS: 315 (M$^+$-31), 177, 145, 113, 59

Elementary Analysis: Found: C, 31.31; H, 2.59%; Calc'd: C, 31.22; H, 2.62%

REFERENCE EXAMPLE 10

0.09 ml of n-butyl mercaptoacetate and 118 mg of 2,6-di-tert-butyl-4-methylpyridine were added to 25 ml of methylene chloride. Then, 300 mg of heptafluoro-n-propylphenyliodonium trifluoromethanesulfonate was added in small amount thereto and the mixture was allowed to react for 20 minutes at room temperature. The precipitate formed was filtered and subjected to column chromatography of silica gel. After eluting iodobenzene with pentane, the desired product was eluted with diethyl ether. Diethyl ether was distilled off from the eluate to obtain n-butyl heptafluoro-n-propylthioacetate as an oily substance. Yield, 87.5%.

$^{19}$F-NMR (CCl$_3$F internal standard in CDCl$_3$): CF$_{3(\gamma)}$—CF$_{2(\beta)}$—CF$_{2(\alpha)}$—S—-80.71 ppm (t, $J_{F\gamma, F\alpha}=9.5$ Hz, CF$_3$), -89.52 ppm (q.t, $J_{F\alpha, F\beta}=3.5$ Hz, $J_{F\alpha,}$ $_{F\gamma}=9.5$ Hz, CF$_{2\alpha}$), -124.7 ppm (t, $J_{F\alpha, F\beta}=3.5$ Hz, CF$_{2\beta}$)

$^1$H-NMR (in CDCl$_3$):

n-C$_3$F$_7$S—CH$_2$—CO$_2$—CH$_2$—CH$_2$—CH$_2$—CH$_3$
(a)      (b)  (c)  (d)

0.93 ppm (m, CH$_3$, 3H), 1.2–1.8 ppm (m, H$_c$, H$_d$, 4H), 3.67 ppm (s, H$_a$, 2H), 4.16 ppm (t, $J_{Hb, Hc}=6$ Hz, H$_b$, 2H)

IR (neat): 2960, 2880, 1745, 1460, 1410, 1380, 1340, 1300, 1280, 1210, 1190, 1110, 1090, 1040, 930, 860, 740, 675 cm$^{-1}$

MS: 215 (+$CH_2$SC$_3$F$_7$), 169, 69, 57, 56

Elementary Analysis: Found: C, 34.27; H, 3.37%; Calc'd: C, 34.18; H, 3.51%

REFERENCE EXAMPLE 11

0.02 ml of n-butyl mercaptoacetate and 28 mg of 2,6-di-tert-butyl-4-methylpyridine were added to 1.5 ml of methylene chloride. Then, 64.6 mg of heptafluoro-n-propyl-p-tolyliodonium methanesulfonate was added thereto and the mixture was allowed to react for 20 minutes at room temperature to obtain n-butyl heptafluoro-n-propylthioacetate. Yield, 97%.

REFERENCE EXAMPLE 12

0.02 ml of n-butyl mercaptoacetate and 27.7 mg of 2,6-di-tert-butyl-4-methylpyridine were added to 1.5 ml of methylene chloride. Then, 71.5 mg of heptafluoro-n-propyl-p-tolyliodonium benzenesulfonate was added thereto, and the mixture was allowed to react for 30 minutes at room temperature to obtain n-butyl pentafluoro-n-propylthioacetate. Yield, 95%.

REFERENCE EXAMPLE 13

0.11 ml of n-butyl mercaptoacetate and 0.062 ml of pyridine were added to 3.5 ml of methylene chloride. Then, 400 mg of heptafluoro-n-propylphenyliodonium trifluoromethanesulfonate was added to the mixture and the resulting mixture was allowed to react for 10 minutes at room temperature to obtain n-butyl heptafluoro-n-propylthioacetate. Yield, 60%.

REFERENCE EXAMPLE 14

3 ml of methylene chloride, 0.046 ml of mercaptoacetic acid and 0.05 ml of pyridine were charged in a flask, and 377 mg of tridecafluoro-n-hexylphenyliodonium trifluoromethanesulfonate was added thereto in small portions while stirring at room temperature, followed by allowing the mixture to react for 20 minutes at room temperature. The reaction mixture was subjected to silica gel column chromatography, and pentane and then diethyl ether were passed through the column. The diethyl ether was then distilled off to obtain 212 mg (92% yield) of tridecafluoro-n-hexylthioacetic acid as white crystals.

Melting Point: 36°–38° C.

$^{19}$F-NMR (CCl$_3$F internal standard in CDCl$_3$): -81.37 ppm (t, J=10 Hz, CF$_3$), -88.46 ppm (m, —SCF$_2$—), -120.2 ppm (m, CF$_2$), -121.9 ppm (m, CF$_2$), -123.2 ppm (m, CF$_2$), -126.5 ppm (m, CF$_2$).

$^1$H-NMR (in CDCl$_3$): 3.73 ppm (s, CH$_2$)

IR (nujol): 1720, 1300, 1240, 1200, 1140, 1080, 1040, 1020, 930, 900, 850, 800, 780, 760, 750, 720, 690, 660, 630, 600, 560, 530 cm$^{-1}$.

MS: 410 (M+), 365, 169, 141, 119, 69, 47, 45.
Elementary Analysis: Found: C, 23.44; H, 0.75%; Calc'd: C, 23.43; H, 0.74%

REFERENCE EXAMPLE 15

3 ml of methylene chloride, 0.04 ml of mercaptoacetic acid and 0.045 ml of pyridine were charged in a flask, and 306 mg of pentadecafluoro-n-heptylphenyliodonium trifluoromethanesulfonate was added thereto in small portions while stirring at room temperature, followed by allowing the mixture to react for 20 minutes at room temperature. The reaction mixture was subjected to silica gel column chromatography, and pentane and then diethyl ether were passed through the column. The diethyl ether was then distilled off to obtain 119 mg (61% yield) of pentadecafluoro-n-heptylthioacetic acid as white crystals.

Melting Point: 48°–50° C.

19F-NMR (CCl3F internal standard in CDCl3): -81.35 ppm (t, $J_{CF3, CF2}$=10 Hz, CF3), -88.37 ppm (t, $J_{CF2, CF2}$=13 Hz, -SCF2-), -120.2 ppm (m, CF2), -121.6 ppm (m, CF2), -122.4 ppm (m, CF2), -123.2 ppm (m, CF2), -126.5 ppm (m, CF2).

1H-NMR (in CDCl3): 3.73 ppm (s, CH2).

IR (nujol): 1710, 1320, 1300, 1240, 1190, 1140, 1100, 985, 930, 900, 830, 800, 780, 750, 720, 700, 670, 645, 560, 530 cm−1.

MS: 460 (M+), 415, 169, 141, 119, 69, 47, 45

Elementary Analysis: Found: C, 23.79; H, 0.70%; Calc'd: C, 23.49; H, 0.66%

REFERENCE EXAMPLE 16

2.0 ml of methylene chloride, 0.03 ml (0.42 mmol) of mercaptoacetic acid and 80 mg (0.39 mmol) of 2,6-di-tert-butyl-4-methylpyridine were charged in a flask, and 290 mg (0.38 mmol) of heptadecafluoro-n-octylphenyliodonium trifluoromethanesulfonate was added thereto in small portions while stirring at room temperature, followed by stirring for 20 minutes at room temperature. The resulting preciptiate was filtered, subjected to silica gel column chromatography and, after eluting iodobenzene with pentane, the desired product was eluted with diethyl ether. Diethyl ether was distilled off from the eluate to obtain heptadecafluoro-n-octylthioacetic acid as white crystals. A sample of the product was purified by gas chromatography. Yield, 88%.

Melting Point: 68°–70° C.

19F-NMR (CCl3F internal standard in CD3CN): -80.26 ppm (t, $J_{CF3, CF2}$=12 Hz, CF3, 3F), -87.14 ppm (br. t, $J_{CF2,CF2}$=12 Hz, —CF2, 2F), -119.0 ppm (br. s, CF2, 2F), -120–121 ppm (br. s, CF2×3, 6F), -121.7 ppm (br. s, CF2, 2F).

1H-NMR (in CD3CN) (60 MHz): 3.88 ppm (s, —CH2—), 3~4 ppm (br.s, —COOH).

IR (nujol): 3000 (broad absorption), 1710, 1330, 1300, 1240, 1210, 1140, 1110, 1090, 940, 800, 780, 720, 700, 655, 575, 560, 530 cm−1.

MS: 510 (M+), 465, 231, 229, 181, 169, 141, 131, 119, 113, 97, 69, 63, 47, 46, 45.

Elementary Analysis: Found: C, 23.52; H, 0.56%; Calc'd: C, 23.54; H, 0.59%

REFERENCE EXAMPLE 17

2.0 ml of methylene chloride, 0.04 ml (0.4–0.5 mmol) of allylmercaptan and 79 mg (0.39 mmol) of 2,6-di-tert-butyl-4-methylpyridine were charged in a flask which had been purged with argon, and 275 mg (0.38 mmol) of heptadecafluoro-n-octylphenyliodonium trifluoromethanesulfonate was added thereto while stirring at room temperature, followed by stirring for 10 minutes at room temperature. The resulting white precipitate was filtered, subjected to column chromatography of silica gel and eluted with pentane. Pentane was distilled off from the eluate and the residue was purified by gas chromatography to obtain heptadecafluoro-n-octylallylthioether as an oily substance. Yield, 22%.

19F-NMR (CCl3F internal standard in CDCl3): -81.32 ppm (t, $J_{CF2,CF3}$=10 Hz, CF3), -87.74 ppm (t, $J_{CF2,CF2}$=12 Hz, α-CF2), -120.2 ppm (m, CF2), -121.6 ppm (m, CF2), -122.2 ppm (m, CF2×2), -123.0 ppm (m, CF2), -126.5 ppm (m, CF2).

1H-NMR (in CDCl3):

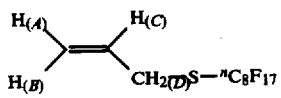

3.63 ppm (br. d, $J_{HC,HD}$=7 Hz, $H_D$, 2H), 5.25 ppm (br. d, $J_{HA,HC}$=10 Hz, $H_A$, 1H), 5.35 ppm (br.d, $J_{HB,HC}$=16.5 Hz, $H_B$, 1H), 5.95 ppm (d.d.t, $J_{HA,HC}$=10 Hz, $J_{HB, HC}$=16.5 Hz, $J_{HC,HD}$=7 Hz, $H_C$, 1H).

IR (neat): 3090, 1640, 1410, 1370, 1350, 1320, 1240, 1210, 1145, 1130, 1110, 1090, 1020, 980, 955, 930, 825, 810, 800, 780, 760, 745, 730, 725, 700, 670, 650, 640, 560, 530 cm−1.

MS: 492 (M+), 123, 73, 69, 41, 39

Elementary Analysis: Found C, 26.97; H, 1.14%; Calc'd: C, 26.84; H, 1.02%

REFERENCE EXAMPLE 18

3 ml of methylene chloride, 0.036 ml of mercaptoacetic acid and 0.04 ml of pyridine were charged in a flask, and 384 mg of heneicosafluoro-n-decylphenyliodonium trifluoromethanesulfonate was added thereto while stirring at room temperature, followed by allowing the mixture to react for 30 minutes at room temperature. The reaction mixture was subjected to silica gel column chromatography, and pentane and then diethyl ether were passed through the column. The diethyl ether was then distilled of to obtain 240 mg (89% yield) of heneicosafluoro-n-decylthioacetic acid.

Melting Point: 109°–111° C.

19F-NMR (CCl3F internal standard in acetone-d6): -80.0 ppm (t, $J_{CF3,CF2}$=10 Hz, CF3), -86.6 ppm (m, -SCF2-), -116~-121 ppm (m, CF2×7), -124 ppm (m, CF2).

1H-NMR (in CDCl3): 3.74 ppm (s, —CH2—),

IR (nujol): 1710, 1300, 1200, 1145, 1110, 1090, 1060, 1035, 970, 935, 890, 860, 770, 720, 665, 650, 630, 555, 530, cm−1.

What is claimed is:

1. Perfluoroalkyl compounds represented by the formula (I):

wherein $R_f$ represents a perfluoroalkyl group having 1 to 20 carbon atoms, Ar represents a substituted or unsubstituted phenyl group wherein the substituent is an alkyl group having 1 to 4 carbon atoms or a halogen atom, I represents an iodine atom, and A represents a hydroxy group or a halogen atom.

* * * * *